(12) United States Patent
Perring et al.

(10) Patent No.: US 8,784,784 B2
(45) Date of Patent: Jul. 22, 2014

(54) ORGANIC COMPOUNDS

(75) Inventors: Keith Douglas Perring, Ashford (GB); John Martin Behan, Ashford (GB); Alan Forbes Provan, Ashford (GB)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 13/636,367

(22) PCT Filed: Apr. 12, 2011

(86) PCT No.: PCT/EP2011/055725
§ 371 (c)(1),
(2), (4) Date: Nov. 9, 2012

(87) PCT Pub. No.: WO2011/128340
PCT Pub. Date: Oct. 20, 2011

(65) Prior Publication Data
US 2013/0058881 A1    Mar. 7, 2013

(30) Foreign Application Priority Data
Apr. 12, 2010 (GB) .................................. 1006042.4

(51) Int. Cl.
*A61K 8/35* (2006.01)
*A61K 8/40* (2006.01)
*A61Q 15/00* (2006.01)

(52) U.S. Cl.
USPC ........................................... 424/65; 424/76.1

(58) Field of Classification Search
CPC ......... A61K 8/35; A61K 8/40; A61K 8/4926; A61K 2300/00; A61Q 15/00; C11B 9/0023
USPC .................................................. 424/65, 76.1
See application file for complete search history.

(56) References Cited

U.S. PATENT DOCUMENTS

| | | | |
|---|---|---|---|
| 4,235,824 A | 11/1980 | Traas et al. | |
| 5,380,707 A * | 1/1995 | Barr et al. | 512/17 |
| 2006/0154851 A1 | 7/2006 | Munro | |

FOREIGN PATENT DOCUMENTS

| | | | |
|---|---|---|---|
| EP | 1063229 A1 | 12/2000 | |
| GB | 2013493 A | 8/1979 | |
| GB | 1572949 A | 8/1980 | |
| WO | 2004048336 A1 | 6/2004 | |
| WO | WO2010000083 | * | 1/2010 |
| WO | 2011128340 A3 | 10/2011 | |

OTHER PUBLICATIONS

Schreiber, "Perfumes," Kirk-Othmer Encyclopedia of Chemical Technology, Sep. 23, 2005.*
GB Search Report for GB1006042.4 dated Jul. 30, 2010.
Written Opinion of the International Searching Authority for PCT/EP2011/055725 dated Jan. 22, 2013.
International Preliminary Report on Patentability for PCT/EP2011/055725 dated Jan. 22, 2013.

* cited by examiner

*Primary Examiner* — Rachael E Bredefeld
(74) *Attorney, Agent, or Firm* — Norris McLaughlin & Marcus PA

(57) ABSTRACT

Deodorant composition for the treatment of female malodour comprising a perfume containing violet nitrile and optionally pharaone and/or zinarine.

4 Claims, No Drawings

ORGANIC COMPOUNDS

This is an application filed under 35 USC 371 of PCT/EP2011/055725.

The present invention is concerned with compositions and methods useful in deodorancy.

A wide variety of technologies exist for delivering deodorant effects to the human axillae. These include numerous inventions claiming deodorancy via fragrance. However, these technologies addressing the problem of underarm odour usually do not discriminate between male and female.

One disclosure that does focus on gender-specific deodorancy is WO03/061609. The compositions and methods disclosed therein rely on the use of so-called "cross-adapting" agents. Cross-adapting agents are odourants that compete with malodorous materials for olfactory receptor sites, or otherwise interfere with the brain circuitry responsible for processing odourant signals such that a subject is desensitized to malodorous materials.

The problem with using cross-adapting agents that are odourants is that, in addition to reducing or eliminating malodour, they may exert an unwanted hedonic effect on a deodorant composition.

There remains a need to provide effective deodorant compositions, in particular those that are gender-specific and which employ materials that do not adversely affect the hedonics of the deodorant composition to which they are applied.

The applicant has surprisingly found that the addition of violet nitrile to a deodorant composition is effective at reducing the perception of malodour from sweat, in particular female sweat.

In a first aspect the invention provides a deodorant composition comprising violet nitrile.

In another aspect of the invention there is provided a female-specific deodorant composition comprising violet nitrile.

In another aspect of the invention there is provided a method of reducing the perception of malodour, comprising administering a deodorant composition that contains violet nitrile.

In yet another aspect of the invention there is provided the use of violet nitrile in a deodorant composition for reducing the perception malodour.

Without prejudice to the generality of the term "reducing the perception of malodour", the term refers in particular to reducing the perception of female malodour, still more particularly female axillary malodour.

As used herein, a deodorant composition refers to an article or a composition applied to an article that is used to reduce the perceived intensity or to block malodour, in particular human axillary malodour and more particularly female axillary malodour. The deodorant composition may be used for a locality such as human axillae, a bathroom, a linen basket, a personal locker or a room such as a gymnasium or the like. Deodorant compositions may be distributed or dispersed in or around said locality by spraying, evaporating or by any other suitable means of application of said composition. Suitable articles for application of the deodorant compositions are known in the art and include, for example, deo-sprays, deo-sticks, air-fresheners, candles and the like.

Violet nitrile, or (2Z,6E)-nona-2,6-dienenitrile is a known fragrance material having an odour in 10% dipropylene glycol that has been described as green violet. It has been suggested for use at no more than 0.01% to about 0.02% by weight of a perfume.

Violet nitrile may be applied singly to a deodorant composition, or it may be applied to said deodorant composition as part of a perfume. The invention provides in another of its aspects a perfume comprising violet nitrile and the use of said perfume in a deodorant composition for reducing the perception of malodour.

Violet nitrile may comprise up to 100% of the perfume for use in a deodorant composition, that is, it may be used as the sole ingredient of a perfume or it may be employed as one ingredient in a perfume composition containing other ingredients.

As violet nitrile is an odourant, the limit on the amount one might employ in a perfume is dictated by the particular hedonic that is sought for the perfume and the hedonic effect violet nitrile will exert. Violet nitrile may be employed at levels exceeding 0.01% or even 0.02% ww based on the perfume, although given its odourant effect this is only recommended where the particular hedonic effect of violet nitrile is desirable.

Of course, it may not be desirable, from a hedonic perspective, in all cases to design perfumes for deodorant compositions that contain high amounts of violet nitrile and its use may be limited by this consideration. However, applicant surprisingly found that violet nitrile can be used in a perfume in amounts of 0.01% ww or less, more particularly 0.01 to 0.001% ww of a perfume, still more particularly 0.005 to 0.002% ww, if used in admixture in said perfume with zinarine and/or pharaone. Zinarine (2-(2,4-dimethylcyclohexyl)pyridine) may be used in amounts of at least 0.05% ww of the perfume, more particularly 0.1 to 0.3% ww. Pharaone may be used in amounts of at least 0.005% ww, more particularly 0.075 to 0.03% ww of the perfume.

Perfumes for use in deodorant compositions for reducing the perception of malodour containing violet nitrile and pharaone and/or zinarine form a particular aspect of the invention. Still more particularly, perfumes containing violet nitrile and pharaone form an aspect of this invention. Still more particularly, perfumes containing violet nitrile and pharaone, at concentrations of at least 0.002% and 0.005% respectively form another aspect of this invention. Even more particularly, perfumes containing 0.005% Violet Nitrile and 0.005% Pharaone form another aspect of this invention.

In addition to violet nitrile and zinarine and/or pharaone, the perfume may also comprise carrier materials; a perfumery base; and other adjuvants useful in perfumes.

The term "carrier materials" as used herein refers to materials that are neutral or practically neutral from a fragrance point of view, that is, the material does not significantly alter the organoleptic properties of perfumes.

As carrier materials one can mention, an emulsifying system, i.e. a solvent and a surfactant system, or a solvent commonly used in perfumery. A detailed description of the nature and type of solvents commonly used in perfumery cannot be exhaustive. However, one can cite as non-limiting examples of solvents useful in perfumery dipropyleneglycol, diethyl phthalate, isopropyl myristate, benzyl benzoate, 2-(2-ethoxyethoxy)-1-ethanol or tri-ethyl citrate.

Carrier materials may also include solids or semi-solids such as absorbing gums or polymers, or encapsulating materials. Encapsulation is a well known process to a person skilled in the art, and may be performed, for instance, using techniques such as spray-drying, agglomeration or wet extrusion, or by coacervation or complex coacervation techniques. To the extent that perfumes described herein contain any solids or semi-solids, it is understood that the concentrations provided herein for violet nitrile, pharaone and zinarine refer to the concentrations of these ingredients based on the total weight of liquid state ingredients in said perfumes.

The term "perfumery base" as used herein means a composition comprising at least one perfuming co-ingredient that is different from a violet nitrile, zinarine and pharaone.

Moreover, the co-ingredients are used to impart a hedonic effect. For example, such a co-ingredient, if it is to be considered as being a perfuming co-ingredient, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect.

In general terms, perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

The term "adjuvant" as used herein means an ingredient that affects the performance of a perfume other than its hedonic performance. For example, an adjuvant may be an ingredient that acts as an aid to processing a perfume or article containing a perfume, or it may improve handling or storage of said perfume or article. It might also be an ingredient that provides additional benefits such as imparting colour or texture to a perfume or article. It might also be an ingredient that imparts light resistance or chemical stability to one or more ingredients contained in the perfume or article. A detailed description of the nature and type of adjuvant commonly used in perfumery or deodorancy cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

As described herein, the perfume can be used in deodorancy for reducing the perception of malodour. The perfume may be applied to a subject or it may be incorporated into a deodorant composition. A deodorant composition containing said perfume forms another aspect of this invention.

The nature and type of the constituents of a deodorant composition, in addition to the perfume do not warrant a more detailed description here, which in any case would not be exhaustive, the skilled person being able to select them on the basis of its general knowledge and according to the nature and the desired effect of said product.

Examples of suitable deodorant composition include articles such as deodorant or anti-perspirant sticks, deodorant or anti-perspirant sprays, soaps, detergents and fabric softeners as well as shower or bath salts, mousses, oils or gels, hygiene products or hair care products such as shampoos, body-care products, air fresheners and also cosmetic preparations. Deodorant compositions may also be applied to substrates or surfaces such as fabrics to exert a malodour counteracting effect. Other deodorant compositions may be fabric refreshers, ironing waters, papers, wipes or the like.

Some of the deodorant compositions mentioned hereinabove may contain aggressive media for one or more ingredients of the perfume of the present invention, so that it may be necessary to protect any of the ingredients from premature decomposition, for example by encapsulation or by chemical modification, such as forming stable precursors of ingredients.

The proportions in which the perfume can be incorporated into the various aforementioned deodorant compositions may vary within a wide range of values. These values are dependent on the nature of the deodorant composition to be perfumed and on the desired organoleptic effect as well as the nature of the co-ingredients in a given base. Typical concentrations for personal care products would be in the order of 0.3% to 3% by weight, or even more, of the perfume based on the weight of the deodorant composition into which they are incorporated. For household care products, the amounts may vary more widely, such as 0.01% to about 20%. Indeed in certain applications such as in electrical air-fresheners, the amount of perfume may be 100% of the deodorant composition.

There now follows a series of examples that illustrate the invention.

EXAMPLE 1

In Vitro-Testing

A trained sensory panel consisting of over 25 members was used to assess each sample, which was presented in random order. At least 30 assessments were made per sample, comprising fragrance mixes consisting of 10% dilutions of each perfume in an odourless/low odour solvent, diethyl phthalate (DEP).

All assessments reported in the examples were carried out in a purpose built panel suite. The suite is designed so that all external distractions (i.e. odour, noise, movement) were eliminated, and the panelists were not distracted during testing.

The fragrance mix and malodour were placed alongside each other in a 500 ml glass vessel. 80 $\mu$l malodour was applied evenly onto a cotton pad (5.5 cm diameter) and the pad placed on top of a squat 15 ml jar alongside a fragrance mix (1 ml in a 15 ml upright jar). Equivalent jars containing DEP in place of fragrance mix were prepared using the same process. The vessel was closed and allowed to equilibrate for half an hour before assessment.

Each panel member assessed each sample for the intensity of malodour and perfume material that could be perceived in the headspace of the glass vessel using a line scale anchored at the extremes (0-100). The malodour control was used as a standard (perceived intensity 75) against which all other perceived intensities were scaled. The scores for each of the panelists were normalised and averaged to give a consensus score across the whole panel.

TABLE 1

Fragrance formulations for Sensory testing:

| | CODE FIP | | | | | | | | |
|---|---|---|---|---|---|---|---|---|---|
| | 25 | 26 | 27 | 28 | 29 | 30 | 31 | 32 | 33 |
| Violet Nitrile (10%) | 0.1 | | | 0.2 | | | 0.1 | 0.1 | |
| Pharaone (10%) | | 0.1 | | | 0.2 | | 0.1 | | 0.1 |
| Zinarine | | | 0.1 | | | 0.2 | | 0.1 | 0.1 |
| Base fragrance 1 | 99.9 | 99.9 | 99.9 | 99.8 | 99.8 | 99.8 | 99.8 | 99.8 | 99.8 |

TABLE 2

Sensory Test Results against Female Sweat Odour

| Fragrance Code | Female Sweat Malodour Intensity | Significance (Fisher)* |
|---|---|---|
| FIP 32 | 37.9 | A |
| FIP 31 | 39.0 | A |
| FIP 28 | 40.2 | A |
| FIP 25 | 51.4 | B |
| FIP 26 | 52.1 | BC |
| FIP 30 | 56.7 | BC |
| BASE | 58.1 | BC |
| FIP 33 | 59.0 | BCD |
| FIP 27 | 60.1 | BCD |
| FIP 29 | 61.3 | CD |
| Control (malodour only) | 67.9 | D |

*Results with the same letter are not significantly different ($p < 0.05$)

Fragrances containing either:

0.1% Violet Nitrile (10%), or 0.1% Pharaone (10%) or 0.1% Zinarine (FIP 25, 26 and 27 respectively);

or 0.2% Pharaone (10%) or 0.2% Zinarine (FIP 29 and 30 respectively);

or 0.1% Pharaone (10%)+0.1% Zinarine (FIP 33)

performed similarly to the base fragrance in terms of reduction of female sweat odour i.e. no significant difference or improvement in the performance of the base fragrance.

However FIP 28 [0.2% Violet Nitrile (10%)], FIP 31 [0.1% Violet Nitrile (10%)+0.1% Pharaone (10%)] and FIP 32 (0.1% Violet Nitrile (10%)+0.1% Zinarine) did perform significantly better than the base fragrance and all other test fragrances in terms of reduction of female sweat odour. There was no significant difference between these three fragrances thus the combination of 0.1% Violet Nitrile (10%) with either 0.1% of Pharaone (10%) or Zinarine performed as well as a fragrance containing 0.2% Violet Nitrile (10%). This would indicate a synergy between Violet Nitrile and Pharaone or Zinarine.

In addition expert evaluations indicate that 0.2% of Violet Nitrile (10%) in a fragrance is hedonically limiting, however the combination of 0.1% Violet Nitrile (10%) and either Pharaone (10%) of Zinarine is more hedonically acceptable.

EXAMPLE 2

In Vivo-Testing

Perfume compositions were made and tested for deodorant action in underarm products, using an Odour Reduction Value test as described in U.S. Pat. No. 4,278,658. The test was carried out using 36 Caucasian female subjects treated with alcoholic deodorant comprising less than 1% w/w of the perfume under investigation, each panelist was sprayed for 2 seconds in the axillae. Fragrance 'G' was a commercial quality perfume known to have high deodorant efficacy. Fragrance 'H' was the result of adding small quantities of Violet Nitrile and Pharaone (see Table 3) to Fragrance G. The perfumes were tested at equal-cost dosages of 0.95% (G) and 0.7% (H).

TABLE 3

Fragrance formulations for Underarm testing:

| | CODE | |
|---|---|---|
| | G | H |
| Violet Nitrile 10% | | 0.05 |
| Pharaone 10% | | 0.1 |
| Base fragrance 2 | 100 | 99.85 |

TABLE 4

Underarm female panel results (5 hours)

| Fragrance Code | Underarm Sweat Malodour Intensity |
|---|---|
| H @0.7% | 1.05 |
| G @ 0.95% | 1.20 |

The malodour intensity scale employed by the assessors ran from 0 to 5, with 5 as the highest level of malodour, the intensity being anchored to standard solutions containing specific concentrations of the malodorous acid, isovaleric acid (see Table 5)

TABLE 5

Standard malodour intensities

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | .57 |

The results in Table 4 indicate that fragrance H performed better in terms of sweat malodour reduction even when dosed at a lower level. The addition of even small amounts of the materials of the invention can improve the deodorant action on females of already highly active perfumes.

The invention claimed is:

1. A method of reducing the perception of female malodour, the method comprising the step of:

applying a deodorant composition comprising a perfume containing violet nitrile and pharaone and/or 2-(2,4-dimethylcyclohexyl)pyridine to human axillae, a bathroom, a linen basket, a personal locker or a room gymnasium.

2. A method of reducing the perception of malodour according to claim 1, wherein the deodorant composition is applied to female human axillae.

3. A method of reducing the perception of female malodour, the method comprising the step of:

applying to human female axillae a deodorant composition comprising a perfume containing violet nitrile and pharaone and/or 2-(2,4 dimethylcyclohexyl)pyridine in an amount effective to reduce the perception of female malodour.

4. A method according to claim 3, wherein the deodorant composition comprises a perfume constituent which comprises violet nitrile in an amount of 0.002% by weight of the perfume constituent, and pharaone in an amount of 0.005% by weight of the perfume constituent.

* * * * *